(12) United States Patent
Campbell

(10) Patent No.: US 12,268,679 B1
(45) Date of Patent: Apr. 8, 2025

(54) COMPOSITIONS AND METHODS FOR EPIDURAL ADMINISTRATION OF MCOPPB FOR PAIN RELIEF

(71) Applicant: Centrexion Therapeutics Corporation, Boston, MA (US)

(72) Inventor: James N. Campbell, Baltimore, MD (US)

(73) Assignee: Centrexion Therapeutics Corporation, Boston, MA (US)

(*) Notice: Subject to any disclaimer, the term of this patent is extended or adjusted under 35 U.S.C. 154(b) by 182 days.

(21) Appl. No.: 17/851,175

(22) Filed: Jun. 28, 2022

Related U.S. Application Data

(60) Provisional application No. 63/215,581, filed on Jun. 28, 2021.

(51) Int. Cl.
 *A61K 31/444* (2006.01)
 *A61K 9/00* (2006.01)

(52) U.S. Cl.
 CPC .......... *A61K 31/444* (2013.01); *A61K 9/0021* (2013.01)

(58) Field of Classification Search
 None
 See application file for complete search history.

(56) References Cited

U.S. PATENT DOCUMENTS

| | | | |
|---|---|---|---|
| 11,045,459 | B1 | 6/2021 | Campbell et al. |
| 2014/0171466 | A1 | 6/2014 | Zaveri et al. |
| 2015/0290211 | A1 | 10/2015 | Bosse et al. |
| 2015/0322066 | A1 | 11/2015 | Tanaka et al. |
| 2016/0052913 | A1 | 2/2016 | Bannister et al. |
| 2018/0228797 | A1 | 8/2018 | Bosse et al. |
| 2021/0386728 | A1 | 12/2021 | Campbell et al. |

FOREIGN PATENT DOCUMENTS

| | | |
|---|---|---|
| WO | WO-2017066488 A1 | 4/2017 |
| WO | WO-2019197564 A1 | 10/2019 |

OTHER PUBLICATIONS

Morgan, Anaesth. Intens, Care, vol. 15, pp. 60-67 (Year: 1987).*
Farquhar-Smith et al, British Journal of Pain, vol. 6, No. 1, pp. 25-35, Feb. 2012.*
Adler and Lotz, "Intrathecal pain management: a team-based approach," J Pain Res. Nov. 3, 2017;10:2565-2575.
Chang et al., "Quantitative Signaling and Structure-Activity Analyses Demonstrate Functional Selectivity at the Nociceptin/Orphanin FQ Opioid Receptor," Mol Pharmacol. Sep. 2015;88(3):502-11.
Courteix et al., "Evidence for an exclusive antinociceptive effect of nociceptin/orphanin FQ, an endogenous ligand for the ORL1 receptor, in two animal models of neuropathic pain," Pain. Jul. 2004;110(1-2):236-45.
Cowen et al., "Assessing pain objectively: the use of physiological markers," Anaesthesia. Jul. 2015;70(7):828-47.
Dougherty and Staats, "Intrathecal drug therapy for chronic pain: from basic science to clinical practice," Anesthesiology. Dec. 1999;91(6):1891-918.
Ferrari et al., "In vitro pharmacological characterization of a novel unbiased NOP receptor-selective nonpeptide agonist AT-403," Pharmacol Res Perspect. Aug. 2017;5(4):e00333.
Hayashi et al., "Discovery of 1-[1-(1-methylcyclooctyl)-4-piperidinyl]-2-[(3R)-3-piperidinyl]-1H-benzimidazole: integrated drug-design and structure-activity relationships for orally potent, metabolically stable and potential-risk reduced novel non-peptide nociceptin/orphanin FQ receptor agonist as antianxiety drug," Chem Biol Drug Des. Oct. 2009;74(4):369-81.
Hayashi et al., "Discovery of 1-[1-(1-methylcyclooctyl)-4-piperidinyl]-2-[(3R)-3-piperidinyl]-1H-benzimidazole: integrated drug-design and structure-activity relationships for orally potent, metabolically stable and potential-risk reduced novel non-peptide nociceptin/orphanin FQ receptor agonist as antianxiety drug," Chem Biol Drug Des. Oct. 2009;74(4):369-81 (abstract).
Hayashi et al., "Discovery of {1-[4-(2-{hexahydropyrrolo[3,4-c]pyrrol-2(1H)-yl}-1H-benzimidazol-1-yl)piperidin-1-yl]cyclooctyl}methanol, systemically potent novel non-peptide agonist of nociceptin/orphanin FQ receptor as analgesic for the treatment of neuropathic pain: design, synthesis, and structure-activity relationships," Bioorg Med Chem. Nov. 1, 2010;18(21):7675-99.
Hayashi et al., "Novel non-peptide nociceptin/orphanin FQ receptor agonist, 1-[1-(1-Methylcyclooctyl)-4-piperidinyl]-2-[(3R)-3-piperidinyl]-1H-benzimidazole: design, synthesis, and structure-activity relationship of oral receptor occupancy in the brain for orally potent antianxiety drug," J Med Chem. Feb. 12, 2009;52(3):610-25.
Hayashi et al., "Novel non-peptide nociceptin/orphanin FQ receptor agonist, 1-[1-(1-Methylcyclooctyl)-4-piperidinyl]-2-[(3R)-3-piperidinyl]-1H-benzimidazole: design, synthesis, and structure-activity relationship of oral receptor occupancy in the brain for orally potent antianxiety drug," J Med Chem. Feb. 12, 2009;52(3):610-25(abstract).
Hirao et al., "Pharmacological characterization of the newly synthesized nociceptin/orphanin FQ-receptor agonist 1-[1-(1-methylcyclooctyl)-4-piperidinyl]-2-[(3R)-3-piperidinyl]-1H-benzimidazole as an anxiolytic agent," J Pharmacol Sci. Mar. 2008;106(3):361-8.
Kiguchi et al., "Central N/OFQ-NOP Receptor System in Pain Modulation," Adv Pharmacol. 2016;75:217-43.
National Institutes of Health, "Complex Regional Pain Syndrome," National Insitute of Neurological Disorders and Stroke. Jan. 2017; NIH Pub. No. 17-4173.
Pope and Deer, "Intrathecal drug delivery for pain: a clinical guide and future directions," Pain Manag. 2015;5(3):175-83.
Rauck et al., "Intrathecal gabapentin to treat chronic intractable noncancer pain," Anesthesiology. Sep. 2013;119(3):675-86.
U.S. Food & Drug Administration, "Clinical Outcome Assessment (COA) Compendium," Center for Drug Evanuation and Research. Aug. 2019.

(Continued)

*Primary Examiner* — Zinna Northington Davis
(74) *Attorney, Agent, or Firm* — Dechert LLP

(57) ABSTRACT

The invention provides compositions and methods for epidural administration of the compound MCOPPB or a pharmaceutically acceptable salt thereof for treating pain, such as nociceptive pain suffered by an adult human.

30 Claims, No Drawings

(56) References Cited

OTHER PUBLICATIONS

Vranken et al., "Severe toxic damage to the rabbit spinal cord after intrathecal administration of preservative-free S(+)-ketamine," Anesthesiology. Oct. 2006;105(4):813-8.
Yaksh et al., "Toxicology profile of N-methyl-D-aspartate antagonists delivered by intrathecal infusion in the canine model," Anesthesiology. May 2008;108(5):938-49.
Younger et al., "Pain outcomes: a brief review of instruments and techniques," Curr Pain Headache Rep. Feb. 2009;13(1):39-43.

* cited by examiner

COMPOSITIONS AND METHODS FOR EPIDURAL ADMINISTRATION OF MCOPPB FOR PAIN RELIEF

CROSS-REFERENCE TO RELATED APPLICATIONS

This application claims the benefit of and priority to U.S. Provisional Patent Application Ser. No. 63/215,581, filed Jun. 28, 2021, the contents of which are hereby incorporated by reference in their entirety.

FIELD OF THE INVENTION

The invention provides compositions and methods for epidural administration of the compound MCOPPB or a pharmaceutically acceptable salt thereof for treating pain, such as nociceptive pain suffered by an adult human.

BACKGROUND

Pain can function as a protective mechanism that allows healthy human beings and animals to avoid tissue damage and/or prevent further damage to injured tissue. However, there are many instances in which pain persists beyond its usefulness. Such unnecessary suffering from pain can impair a subject's physical mobility, mental performance, and even contribute to depression.

Substantial resources have been devoted over the years to researching the causes of various types of pain and to the development of medicine to attenuate pain experienced by a patient. Exemplary classes of common pain-relief medications include opioids, non-steroidal anti-inflammatory agents, corticosteroids, and centrally acting agents such as anti-depressants and anti-epileptics. However, existing therapies for treating pain are not effective for all patients and/or can have adverse side effects.

Accordingly, a need exists for improved treatments for pain. The present invention addresses this need and provides other related advantages.

SUMMARY

The invention provides compositions and methods for epidural administration of the compound MCOPPB or a pharmaceutically acceptable salt thereof for treating pain, such as nociceptive pain suffered by an adult human. The methods desirably provide relief from pain for a long duration of time. The methods may be characterized by, for example, the type of pain to be treated, amount of reduction in pain intensity provided by the method, duration of reduction in pain intensity provided by the method, dose of MCOPPB, duration of administration of MCOPPB, and other features. Various aspects and embodiments of the invention are described in further detail below.

Accordingly, one aspect of the invention provides a method for treating pain in a patient. The method comprises epidurally administering to a patient in need thereof a therapeutically effective amount of a pharmaceutical composition comprising (i) MCOPPB or a pharmaceutically acceptable salt thereof and (ii) a pharmaceutically acceptable carrier, to thereby treat the pain. The method may be further characterized according to various features, including the type of pain. Exemplary types of pain include chronic pain, acute pain, nociceptive pain, neuropathic pain, inflammatory pain, arthritic pain, cancer pain, complex regional pain syndrome (e.g., Reflex Sympathetic Dystrophy), trauma pain, pain due to surgery, postoperative pain, back pain, and other types of pain. In certain embodiments, the pain is nociceptive pain. The method may also be further characterized according to the magnitude of reduction in pain achieved, such as where the method achieves at least a 20% reduction, or at least a 40% reduction, in pain intensity relative to pain observed without administering said pharmaceutical composition.

Another aspect of the invention provides a method for locally administering MCOPPB or a pharmaceutically acceptable salt thereof to a patient. The method comprises epidurally administering to a patient in need thereof a pharmaceutical composition comprising (i) MCOPPB or a pharmaceutically acceptable salt thereof and (ii) a pharmaceutically acceptable carrier. The method may be further characterized according to various features, including the dose of MCOPPB administered to the patient. In certain embodiments, the administering delivers a dose of MCOPPB in the range of about 1 mg to 10 mg.

Also provided are pharmaceutical compositions for use in the methods. Also provided are medical kits.

DETAILED DESCRIPTION

The invention provides compositions and methods for epidural administration of the compound MCOPPB or a pharmaceutically acceptable salt thereof for treating pain, such as nociceptive pain suffered by an adult human. The methods desirably provide relief from pain for a long duration of time. The methods may be characterized by, for example, the type of pain to be treated, amount of reduction in pain intensity provided by the method, duration of reduction in pain intensity provided by the method, dose of MCOPPB, duration of administration of MCOPPB, and other features.

MCOPPB is a potent and selective non-peptide agonist for the human nociceptin receptor (hNOPR). MCOPPB displays both high binding affinity for hNOPR (Ki=85 pM; Hayashi et al. in *J. Med. Chem.* 52 (2009) pg 610-625) and high functional potency regarding agonism of hNOPR. In functional assays performed in Chinese Hamster Ovary cells engineered to over-express hNOPR. MCOPPB is a highly potent full agonist of G-protein signaling pathways as measured by both cAMP accumulation ($EC_{50}$=25 pM; See Chang et al. in *Mol. Pharmacol.* 88 (2015) 502-511) and $Ca^{2+}$ mobilization ($EC_{50}$=63 pM; Ferrari et al. in *Pharma. Res. Per.* 5 (2017) e00333). As compared with its potency in activating hNOPR, the functional potency of MCOPPB at the classical opioid receptors is much lower. It typically shows 1,500-fold and 4,000-fold lower potency for the human mu and kappa opioid receptors, respectively, and activates the human delta receptor only a small amount (Ferrari et al. in *Pharma. Res. Per.* 5 (2017) e00333). In animal studies, systemically-administered MCOPPB produces potent anxiolytic effects, with no inhibition of memory or motor function, and only slight sedative side effects which do not appear until much higher doses than the effective anxiolytic dose range (Hirao et al. in *J. Pharmacol. Sci.* 106 (2008) 361-368).

Various aspects of the invention are set forth below in sections; however, aspects of the invention described in one particular section are not to be limited to any particular section.

I. Therapeutic Applications

The invention provides compositions and methods for epidural administration of the compound MCOPPB or a pharmaceutically acceptable salt thereof for treating pain, such as nociceptive pain suffered by an adult human. The method generally comprises epidurally administering to a patient in need thereof a pharmaceutical composition comprising (i) MCOPPB or a pharmaceutically acceptable salt thereof and (ii) a pharmaceutically acceptable carrier. The methods desirably provide relief from pain for long durations of time, with minimal inconvenience to the patient. Various aspects and embodiments of the methods are described below.

First Method

One aspect of the invention provides a method of treating a patient suffering from pain, wherein the method comprises epidurally administering to a patient in need thereof a therapeutically effective amount of a pharmaceutical composition comprising (i) MCOPPB or a pharmaceutically acceptable salt thereof and (ii) a pharmaceutically acceptable carrier, to thereby treat the pain. The therapeutic method may be used to treat various types of pain and may be further characterized by multiple features, as described in more detail below. In certain embodiments, the pharmaceutical composition consists of (i) MCOPPB and (ii) a pharmaceutically acceptable carrier.

Second Method

Another aspect of the invention provides a method of locally administering MCOPPB or a pharmaceutically acceptable salt thereof to a patient, wherein the method comprises epidurally administering to a patient in need thereof a pharmaceutical composition comprising (i) MCOPPB or a pharmaceutically acceptable salt thereof and (ii) a pharmaceutically acceptable carrier. In certain embodiments, the pharmaceutical composition consists of (i) MCOPPB and (ii) a pharmaceutically acceptable carrier. The method may be further characterized by multiple features, as described in more detail below.

Exemplary Additional Features of the First Method

Exemplary additional features of the first method are described below, which include type of pain to be treated, amount of reduction in pain intensity provided by the method, and duration of reduction in pain intensity provided by the method. The invention embraces all permutations and combinations of these features.

Type of Pain

The method may be further characterized according to the type of pain experienced by the patient. Accordingly, in certain embodiments, the pain is chronic pain. In certain other embodiments, the pain is acute pain. In certain embodiments, the pain is nociceptive pain. In certain embodiments, the pain is neuropathic pain. In certain other embodiments, the pain is inflammatory pain. In certain embodiments, the pain is arthritis pain. In certain embodiments, the pain is arthritis pain selected from osteoarthritis pain and rheumatoid arthritis pain.

In certain other embodiments, the pain is pain due to cancer. In certain embodiments, the pain is due to a cancer selected from the group consisting of a solid tumor, leukemia, and lymphoma. In certain embodiments, the pain is due to a cancer selected from the group consisting of a bladder cancer, breast cancer, cervical cancer, colon cancer, colorectal cancer, endometrial cancer, esophageal cancer, leukemia, lung cancer, liver cancer, skin cancer, ovarian cancer, pancreatic cancer, prostate cancer, rectal cancer, renal cancer, stomach cancer, testicular cancer, and uterine cancer.

In certain other embodiments, the pain is complex regional pain syndrome. In certain embodiments, the complex regional pain syndrome is reflex sympathetic dystrophy pain. In certain other embodiments, the pain is trauma pain.

In certain embodiments, the pain is due to surgery. In certain embodiments, the pain is postoperative pain. In certain embodiments, the pain is postoperative pain due to joint replacement surgery. In certain embodiments, the joint replacement surgery is knee joint replacement surgery or hip joint replacement surgery.

In certain embodiments, the pain is located in the patient's hand, wrist, arm, shoulder, back, hip, leg, knee, ankle, foot, or toe. In certain embodiments, the pain is located in the patient's hip. In certain embodiments, the pain is located in the patient's back. In certain embodiments, the pain is located in the patient's leg. In certain embodiments, the pain is located in the patient's knee.

In certain embodiments, the pain is back pain. In certain embodiments, the pain is low back pain. In certain embodiments, the pain is chronic low back pain. In certain embodiments, the pain is leg pain. In certain embodiments, the pain is abdominal pain.

In certain embodiments, the pain is postoperative pain following surgery to remove prostate cancer tissue. In certain embodiments, the pain is pain due to a pinched nerve, a herniated disc, or spinal stenosis.

In certain other embodiments, the pain is a neuropathic pain selected from the group consisting of low back pain, hip pain, leg pain, non-herpetic neuralgia, post-herpetic neuralgia, diabetic neuropathy pain, lumbosacral radiculopathy pain, nerve injury-induced pain, acquired immune deficiency syndrome (AIDS) related neuropathic pain, head trauma pain, phantom limb pain, multiple sclerosis pain, root avulsion pain, painful traumatic mononeuropathy, painful polyneuropathy, thalamic pain syndrome, post-stroke pain, central nervous system injury pain, post-surgical pain, carpal tunnel syndrome pain, trigeminal neuralgia pain, post mastectomy syndrome pain, post-thoracotomy syndrome pain, stump pain, repetitive motion pain, neuropathic pain associated hyperalgesia and allodynia, drug-induced pain, toxin-caused nerve injury pain, chemotherapy-caused nerve injury pain, and combinations thereof.

Amount of Reduction in Pain Intensity

The method may be further characterized according to the amount of reduction in pain intensity relative to pain observed without administering the pharmaceutical composition. Accordingly, in certain embodiments, the method is characterized by achieving at least a 20% reduction in pain intensity relative to pain observed without administering the pharmaceutical composition. In certain embodiments, the method is characterized by achieving at least a 40% reduction in pain intensity relative to pain observed without administering the pharmaceutical composition. In certain embodiments, the method is characterized by achieving at least a 60% reduction in pain intensity relative to pain observed without administering the pharmaceutical composition. In certain embodiments, the method is characterized by achieving at least an 80% reduction in pain intensity relative to pain observed without administering the pharmaceutical composition. In certain embodiments, the method is characterized by achieving at least a 90% reduction in pain intensity relative to pain observed without administering the pharmaceutical composition.

In certain embodiments, the patient's pain intensity is measured using a Visual Analogue Scale (VAS). In certain embodiments, the Visual Analogue Scale (VAS) evaluates pain on a scale ranging from 0 (i.e., no pain) to 10 (i.e., maximum pain). In certain embodiments, the patient's pain intensity prior to receiving treatment is greater than 3 on VAS. In certain embodiments, the patient's pain intensity prior to receiving treatment is greater than 4 on VAS. In certain embodiments, the patient's pain intensity prior to receiving treatment is greater than 5 on VAS. In certain embodiments, the patient's pain intensity prior to receiving treatment is greater than 6 on VAS. In certain embodiments, the patient's pain intensity prior to receiving treatment is greater than 7 on VAS. In certain embodiments, the patient's pain intensity prior to receiving treatment is greater than 8 on VAS. In certain embodiments, the patient's pain intensity prior to receiving treatment is in the range of from 2 to 5 on the VAS. In certain embodiments, the patient's pain intensity prior to receiving treatment is in the range of from 4 to 7 on the VAS. In certain embodiments, the patient's pain intensity prior to receiving treatment is in the range of from 5 to 8 on the VAS. In certain embodiments, the patient's pain intensity prior to receiving treatment is in the range of from 6 to 10 on the VAS.

In certain embodiments, due to receiving MCOPPB according to the invention method, there is a reduction in the patient's pain by at least two on the VAS scale. In certain embodiments, due to receiving MCOPPB according to the invention method, there is a reduction in the patient's pain by at least three on the VAS scale. In certain embodiments, due to receiving MCOPPB according to the invention method, there is a reduction in the patient's pain by at least four on the VAS scale. In certain embodiments, due to receiving MCOPPB according to the invention method, there is a reduction in the patient's pain by at least five on the VAS scale. In certain embodiments, due to receiving MCOPPB according to the invention method, there is a reduction in the patient's pain by at least six on the VAS scale.

Duration of Reduction in Pain Intensity

The method may be further characterized according to the duration of reduction in pain intensity. Accordingly, in certain embodiments, the reduction in pain intensity lasts for at least 3 hours. In certain embodiments, the reduction in pain intensity lasts for at least 4 hours. In certain embodiments, the reduction in pain intensity lasts for at least 6 hours. In certain embodiments, the reduction in pain intensity lasts for at least 8 hours. In certain embodiments, the reduction in pain intensity lasts for at least 10 hours. In certain embodiments, the reduction in pain intensity lasts for at least 12 hours. In certain embodiments, the reduction in pain intensity lasts for at least 18 hours. In certain embodiments, the reduction in pain intensity lasts for at least 1, 2, 3, 4, 5, 6, 7, 8, 9, 10, 11, 12, 13, 14, 15, 16, 17, 18, 19, 20, 21, 22, 23, or 24 hours.

In certain embodiments, the reduction in pain intensity lasts for at least 1, 2, 3, 4, 5, or 6 days. In certain embodiments, the reduction in pain intensity lasts for at least 1 week. In certain embodiments, the reduction in pain intensity lasts for at least 2 weeks. In certain embodiments, the reduction in pain intensity lasts for at least 3 weeks. In certain embodiments, the reduction in pain intensity lasts for at least 4 weeks.

In certain embodiments, the reduction in pain intensity lasts for a duration of 1 to 6 hours. In certain embodiments, the reduction in pain intensity lasts for a duration of 6 to 12 hours. In certain embodiments, the reduction in pain intensity lasts for a duration of 12 to 24 hours. In certain embodiments, the reduction in pain intensity lasts for a duration of from 1 to 2 hours, from 2 to 4 hours, from 4 to 6 hours, from 6 to 8 hours, from 8 to 10 hours, from 10 to 12 hours, from 12 to 16 hours, from 16 to 20 hours, or from 20 to 24 hours. In certain embodiments, the reduction in pain intensity lasts for a duration of 1 to 4 hours. In certain embodiments, the reduction in pain intensity lasts for a duration of 4 to 8 hours.

In certain embodiments, the reduction in pain intensity lasts for a duration of 1 to 3 days. In certain embodiments, the reduction in pain intensity lasts for a duration of 3 to 6 days. In certain embodiments, the reduction in pain intensity lasts for a duration of 6 to 14 days. In certain embodiments, the reduction in pain intensity lasts for a duration of 14 to 21 days. In certain embodiments, the reduction in pain intensity lasts for a duration of 21 to 30 days.

Exemplary Further Features of the First and Second Methods

Exemplary additional features of the first and second methods are described below, which include the dose of MCOPPB, the duration of administration of MCOPPB, aspects of the pharmaceutical composition, aspects of the administration device, and other features. The invention embraces all permutations and combinations of these features.

Dose of MCOPPB

The method may be further characterized according to the dose of MCOPPB administered to the patient. Accordingly, in certain embodiments, the administering delivers a dose of MCOPPB in the range of about 0.1 mg to 15 mg. In certain embodiments, the administering delivers a dose of MCOPPB in the range of about 0.5 mg to 15 mg. In certain embodiments, the administering delivers a dose of MCOPPB in the range of about 0.1 mg to 10 mg, about 1 mg to 10 mg, about 0.1 mg to about 1 mg, about 1 mg to about 2 mg, about 2 mg to about 4 mg, about 4 mg to about 6 mg, about 6 mg to about 8 mg, about 8 mg to about 10 mg, about 10 mg to about 12 mg, or about 12 mg to about 14 mg. In certain embodiments, the administering delivers a dose of MCOPPB in the range of about 0.1, 0.2, 0.3, 0.4, 0.5, 0.6, 0.7, 0.8, 0.9, 1, 2, 3, 4, 5, 6, 7, 8, 9, 10, 11, 12, 13, 14, or 15 mg.

In certain embodiments, the administering delivers a dose of MCOPPB in the range of about 0.1 mg to 10 mg. In certain embodiments, the administering delivers a dose of MCOPPB in the range of about 1 mg to 10 mg. In certain embodiments, the administering delivers a dose of MCOPPB in the range of about 0.1 mg to 0.5 mg. In certain embodiments, the administering delivers a dose of MCOPPB in the range of about 0.5 mg to 1 mg. In certain embodiments, the administering delivers a dose of MCOPPB in the range of about 1 mg to 3 mg. In certain embodiments, the administering delivers a dose of MCOPPB in the range of about 3 mg to 6 mg. In certain embodiments, the administering delivers a dose of MCOPPB in the range of about 6 mg to 8 mg. In certain embodiments, the administering delivers a dose of MCOPPB in the range of about 8 mg to 10 mg. In certain embodiments, the administering delivers a dose of MCOPPB in the range of about 5 mg to 10 mg. In certain embodiments, the administering delivers a dose of MCOPPB in the range of about 5 mg to 8 mg. In certain embodiments, the administering delivers a dose of MCOPPB in the range of about 6 mg to 7 mg.

In certain embodiments, the administering delivers a dose of MCOPPB in the amount of about 100 µg per kg weight of the patient. In certain embodiments, the administering delivers a dose of MCOPPB in the range of from about 90 µg to about 110 µg per kg weight of the patient. In certain embodiments, the administering delivers a dose of MCOPPB in the range of from about 80 µg to about 120 µg per kg weight of the patient. In certain embodiments, the administering delivers a dose of MCOPPB in the amount of about 90, 92, 94, 96, 98, 100, 102, 104, 106, 108, or 110 µg per kg weight of the patient.

If the MCOPPB is administered to the patient in the form of a salt, solvate, or solvate of a salt, then the specified amount of MCOPPB corresponds to the amount of MCOPPB within the salt, solvate, or solvate of salt of MCOPPB administered to the patient.

In certain embodiments, the dose of MCOPPB is administered once per day. In certain embodiments, the dose of MCOPPB is administered twice per day. In certain embodiments, the dose of MCOPPB is administered three times per day. In certain embodiments, the dose of MCOPPB is administered one to three times per day. In certain embodiments, the dose of MCOPPB is administered 3, 4, 5, or 6 times per day.

In certain embodiments, any dose of MCOPPB is administered no sooner than three hours after administration of a prior dose of MCOPPB. In certain embodiments, any dose of MCOPPB is administered no sooner than four hours after administration of a prior dose of MCOPPB.

Duration of Administration of MCOPPB

The method may be further characterized according to the duration of administration of MCOPPB to the patient. Accordingly, in certain embodiments, the pharmaceutical composition is administered continuously by epidural administration over at least 0.5 hours. In certain embodiments, the pharmaceutical composition is administered continuously by epidural administration over at least 1 hour. In certain embodiments, the pharmaceutical composition is administered continuously by epidural administration for at least 4 hours. In certain embodiments, the pharmaceutical composition is administered continuously by epidural administration for at least 6 hours. In certain embodiments, the pharmaceutical composition is administered continuously by epidural administration for at least 8 hours. In certain embodiments, the pharmaceutical composition is administered continuously by epidural administration for at least 12 hours. In certain embodiments, the pharmaceutical composition is administered continuously by epidural administration for at least 16 hours. In certain embodiments, the pharmaceutical composition is administered continuously by epidural administration for at least 20 hours. In certain embodiments, the pharmaceutical composition is administered continuously by epidural administration for from 0.5 hours to 1 hour, 1 hour to 3 hours, 4 hours to 6 hours, 4 hours to 8 hours, 4 hours to 10 hours, 4 hours to 12 hours, 8 hours to 12 hours, 8 hours to 16 hours, 8 hours to 20 hours, 10 hours to 16 hours, 10 hours to 18 hours, 10 hours to 20 hours, 10 hours to 24 hours, or 18 hours to 24 hours.

In certain embodiments, the pharmaceutical composition is administered continuously by epidural administration during at least 10% of the patient's waking hours. In certain embodiments, the pharmaceutical composition is administered continuously by epidural administration during at least 20%, 20%, 40%, 50%, 60%, 70%, 80%, or 90% of the patient's waking hours.

In certain embodiments, the pharmaceutical composition is administered by epidural administration on at least 2 consecutive days. In certain embodiments, the pharmaceutical composition is administered by epidural administration on at least 3 consecutive days. In certain embodiments, the pharmaceutical composition is administered by epidural administration on at least 4 consecutive days. In certain embodiments, the pharmaceutical composition is administered by epidural administration on from about two to about seven consecutive days. In certain embodiments, the pharmaceutical composition is administered by epidural administration on from about fourteen to about twenty-one consecutive days.

In certain embodiments, the pharmaceutical composition is administered by epidural administration on at least 2 days during a 7 day period. In certain embodiments, the pharmaceutical composition is administered by epidural administration on at least 3 days during a 7 day period. In certain embodiments, the pharmaceutical composition is administered by epidural administration on at least 4 days during a 7 day period. In certain embodiments, the pharmaceutical composition is administered by epidural administration on at least 5 days during a 7 day period.

In certain embodiments, the pharmaceutical composition is administered by epidural administration on at least 3 days during a 14 day period. In certain embodiments, the pharmaceutical composition is administered by epidural administration on at least 4 days during a 14 day period. In certain embodiments, the pharmaceutical composition is administered by epidural administration on at least 5 days during a 14 day period. In certain embodiments, the pharmaceutical composition is administered by epidural administration on at least 7 days during a 14 day period. In certain embodiments, the pharmaceutical composition is administered by epidural administration on at least 10 days during a 14 day period. In certain embodiments, the pharmaceutical composition is administered by epidural administration on at least 12 days during a 14 day period.

In certain embodiments, the dose of MCOPPB is administered as a bolus administration.

In certain embodiments, the pharmaceutical composition is administered continuously by epidural administration at a rate of from about 0.1 to about 0.5 mg per hour. In certain embodiments, the pharmaceutical composition is administered continuously by epidural administration at a rate of from about 0.2 to about 0.4 mg per hour.

In certain embodiments, the pharmaceutical composition is administered by epidural administration below the T8 vertebrae of the patient.

In certain embodiments, when multiple doses of MCOPPB are administered to the patient, a dose of MCOPPB after the first dose of MCOPPB may be adjusted to account for the patient's level of pain. For example, in certain embodiments, the second or subsequent dose of MCOPPB is a smaller amount of MCOPPB relative to the first dose of MCOPPB.

Pharmaceutical Composition and Administration Device

The method may be further characterized according to the pharmaceutical composition, for example, components of the composition or the tonicity of the composition. Accordingly, in certain embodiments, the pharmaceutical composition comprises MCOPPB and water. In certain embodiments, the pharmaceutical composition comprises MCOPPB, water, and an alkali metal salt. In certain other embodiments, the pharmaceutical composition is approximately isotonic.

The pharmaceutical composition may be further characterized according to the stereochemical purity of MCOPPB in the pharmaceutical composition. In certain embodiments, the MCOPPB in the pharmaceutical composition has an enantiomeric excess of at least 80%, 85%, 90%, 95%, 97%, 98%, or 99%. In certain embodiments, the MCOPPB in the pharmaceutical composition has an enantiomeric excess of at least 95%. In certain embodiments, the MCOPPB in the pharmaceutical composition has an enantiomeric excess of at least 98%.

In certain embodiments, MCOPPB in the pharmaceutical composition is in the form of a pharmaceutically acceptable salt, such as a hydrochloride salt.

The method may be further characterized according to the device that is used for the administration. Accordingly, in certain embodiments, the pharmaceutical composition is administered epidurally via a hand-held syringe. In certain embodiments, the pharmaceutical composition is administered epidurally via a pump device. In certain embodiments, when the therapeutic agent is administered epidurally via a pump device, and the pump device is an osmotic pump. In certain embodiments, the therapeutic agent is administered epidurally via a catheter that is fluidically connected to a pump device located outside the patient's body.

The pump device is desirably programmable. Optionally, the pump may respond to patient request, e.g., where the amount and/or rate of pharmaceutical composition administered by the pump device may be influenced by the patient, where, for example, the patient can have the pump device deliver more pharmaceutical composition (e.g., to control breakthrough pain) or less pharmaceutical composition (where pain is less and, therefore, less pharmaceutical composition is needed).

Patients for Treatment

The methods may be further characterized according to the patient to be treated. In certain embodiments, the patient is an adult human. In certain other embodiments, the patient is a pediatric human. In certain other embodiments, the patient is a veterinary animal.

Preparation of a Pharmaceutical Composition Comprising MCOPPB

A pharmaceutical composition comprising (i) MCOPPB or a pharmaceutically acceptable salt thereof and (ii) a pharmaceutically acceptable carrier may be prepared by combining (a) MCOPPB or a pharmaceutically acceptable salt thereof with (b) a pharmaceutically acceptable carrier. In certain instances, MCOPPB used to prepare the pharmaceutical composition is in the form of a pharmaceutically acceptable salt, such as hydrochloride salt. In certain instances, MCOPPB used to prepare the pharmaceutical composition may be in the form of a solvate, such as a hydrate. In certain instances, MCOPPB used to prepare the pharmaceutical composition may be in the form of a solvate of a pharmaceutically acceptable salt, such as a hydrate of MCOPPB hydrochloride salt. One exemplary hydrate of a MCOPPB hydrochloride salt is represented by formula I in which variable x is an integer (e.g., 1, 2, or 3):

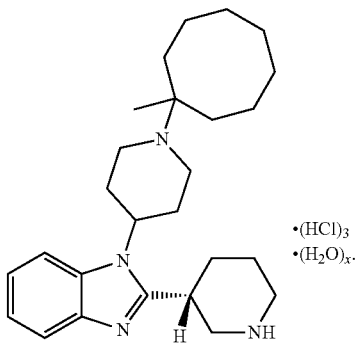

(I)

II. Pharmaceutical Compositions for Epidural Administration

The invention provides pharmaceutical compositions comprising MCOPPB or a pharmaceutically acceptable salt thereof. In certain embodiments, the pharmaceutical compositions comprise (i) MCOPPB or a pharmaceutically acceptable salt thereof, and (ii) a pharmaceutically acceptable carrier. Desirably, the pharmaceutical composition is formulated for epidural administration. In certain embodiments, the pharmaceutical compositions preferably comprise a therapeutically-effective amount of MCOPPB, formulated together with one or more pharmaceutically acceptable carriers.

As described in detail below, the pharmaceutical compositions of the present invention are preferably specially formulated for epidural administration by, for example, epidural injection as, for example, a sterile solution.

Pharmaceutical compositions of this invention suitable for epidural administration may comprise one or more compounds described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain a preservative, sugars, alcohols, antioxidants, buffers, bacteriostats, solutes which render the formulation isotonic with the cerebrospinal fluid of the intended recipient or suspending or thickening agents.

Exemplary suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In general, a suitable dose of a compound of the invention will be that amount of the compound which is the lowest dose effective to produce a therapeutic effect. Such an effective dose will generally depend upon the factors described above. When the compounds described herein are co-administered with another agent (e.g., as sensitizing agents), the effective amount may be less than when the agent is used alone.

The description above describes multiple aspects and embodiments of the invention. The patent application specifically contemplates all combinations and permutations of the aspects and embodiments.

III. Medical Kits

Another aspect of this invention is a kit comprising (i) MCOPPB or a pharmaceutically acceptable salt thereof, and (ii) instructions for epidural administration and/or treating pain, according to procedures described herein.

IV. Definitions

To facilitate an understanding of the present invention, a number of terms and phrases are defined below.

The terms "a" and "an" as used herein mean "one or more" and include the plural unless the context is inappropriate.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "about" as used herein when referring to a measurable value (e.g., weight, time, and dose) is meant to encompass variations, such as ±10%, ±5%, ±1%, or ±0.1% of the specified value.

The compound MCOPPB has the chemical name 1-[1-(1-methylcyclooctyl)-4-piperidinyl]-2-[(3R)-3-piperidinyl]-1H-benzimidazole, which is illustrated by chemical formula:

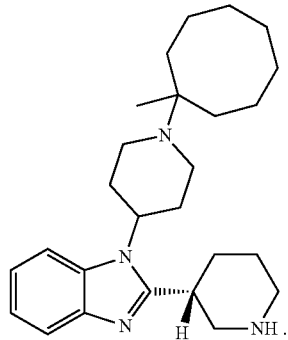 [SMILES: CC1(N2CCC(n3c([C@@H]4CCCNC4)nc4ccccc43)CC2)CCCCCCC1]

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of treating a patient suffering from pain, comprising epidurally administering to a patient in need thereof a therapeutically effective amount of a pharmaceutical composition comprising (i) MCOPPB or a pharmaceutically acceptable salt thereof and (ii) a pharmaceutically acceptable carrier, to thereby treat the pain.

2. The method of claim 1, wherein the pain is chronic pain.

3. The method of claim 1, wherein the pain is acute pain.

4. The method of claim 1, wherein the pain is nociceptive pain.

5. The method of claim 1, wherein the pain is neuropathic pain.

6. The method of claim 1, wherein the pain is inflammatory pain.

7. The method of claim 1, wherein the pain is trauma pain.

8. The method of claim 1, wherein the pain is due to surgery.

9. The method of claim 1, wherein the pain is postoperative pain.

10. The method of claim 1, wherein the pain is complex regional pain syndrome.

11. The method of claim 10, wherein the complex regional pain syndrome is reflex sympathetic dystrophy pain.

12. The method of claim 1, wherein the pain is due to cancer.

13. The method of claim 1, wherein the pain is due to a cancer selected from the group consisting of a solid tumor, leukemia, and lymphoma.

14. The method of claim 1, wherein the pain is due to a cancer selected from the group consisting of a bladder cancer, breast cancer, cervical cancer, colon cancer, colorectal cancer, endometrial cancer, esophageal cancer, leukemia, lung cancer, liver cancer, skin cancer, ovarian cancer, pancreatic cancer, prostate cancer, rectal cancer, renal cancer, stomach cancer, testicular cancer, and uterine cancer.

15. The method of claim 1, wherein the pain is arthritis pain.

16. The method of claim 1, wherein the pain is arthritis pain selected from osteoarthritis pain and rheumatoid arthritis pain.

17. The method of claim 1, wherein the pain is located in the patient's hand, wrist, arm, shoulder, back, hip, leg, knee, ankle, foot, or toe.

18. The method of claim 1, wherein the pain is postoperative pain following surgery to remove prostate cancer tissue.

19. The method of claim 1, wherein the pain is pain due to a pinched nerve, a herniated disc, or spinal stenosis.

20. The method of claim 1, wherein the pain is back pain.

21. The method of claim 1, wherein the pain is low back pain.

22. The method of claim 1, wherein the pain is leg pain.

23. The method of claim 1, wherein the pain is abdominal pain.

24. The method of claim 1, wherein the pain is a neuropathic pain selected from the group consisting of low back pain, hip pain, leg pain, non-herpetic neuralgia, post-herpetic neuralgia, diabetic neuropathy pain, lumbosacral radiculopathy pain, nerve injury-induced pain, acquired immune deficiency syndrome (AIDS) related neuropathic pain, head trauma pain, phantom limb pain, multiple sclerosis pain, root avulsion pain, painful traumatic mononeuropathy, painful polyneuropathy, thalamic pain syndrome, post-stroke pain, central nervous system injury pain, post-surgical pain, carpal tunnel syndrome pain, trigeminal neuralgia pain, post mastectomy syndrome pain, post-thoracotomy syndrome pain, stump pain, repetitive motion pain, neuropathic pain associated hyperalgesia and allodynia, drug-induced pain, toxin-caused nerve injury pain, chemotherapy-caused nerve injury pain, and combinations thereof.

25. The method of claim 1, wherein the method is characterized by achieving at least a 60% reduction in pain intensity relative to pain observed without administering said pharmaceutical composition.

26. The method of claim 1, wherein the method is characterized by achieving at least an 80% reduction in pain intensity relative to pain observed without administering said pharmaceutical composition.

27. A method of locally administering MCOPPB or a pharmaceutically acceptable salt thereof to a patient, comprising epidurally administering to a patient in need thereof a pharmaceutical composition comprising (i) MCOPPB or a pharmaceutically acceptable salt thereof and (ii) a pharmaceutically acceptable carrier.

28. The method of claim 1, wherein the administering delivers a dose of MCOPPB in the range of about 0.1 mg to 15 mg.

29. The method of claim 1, wherein the administering delivers a dose of MCOPPB in the range of about 1 mg to 10 mg.

30. The method of claim 1, wherein the patient is an adult human.

* * * * *